United States Patent [19]

Strom et al.

[11] Patent Number: 5,152,980
[45] Date of Patent: Oct. 6, 1992

[54] INDUCTION OF TOLERANCE TO A FOREIGN ANTIGEN IL-2 RECEPTOR-BINDING SUBSTANCES

[75] Inventors: Terry B. Strom; Vicki E. Kelley, both of Brookline, Mass.

[73] Assignees: The Beth Israel Hospital Association; Brigham and Women's Hospital, both of Boston, Mass.

[21] Appl. No.: 353,865

[22] Filed: May 18, 1989

Related U.S. Application Data

[63] Continuation-in-part of Ser. No. 196,036, May 19, 1988, abandoned.

[51] Int. Cl.[5] .................. A61K 39/00; A61K 37/02
[52] U.S. Cl. ........................... 424/85.2; 424/85.1; 424/85.8; 424/85.91; 424/88; 424/92; 424/89; 424/90; 424/91; 514/885; 514/2; 530/351; 530/388.22; 530/388.75
[58] Field of Search ................ 424/88-92, 424/85.1, 85.2, 85.8, 85.91; 514/885; 530/351, 387

[56] References Cited

U.S. PATENT DOCUMENTS

| | | | |
|---|---|---|---|
| 4,545,985 | 10/1985 | Pastan et al. | 424/88 |
| 4,675,382 | 6/1987 | Murphy | 530/350 |
| 4,681,760 | 7/1987 | Fathman | 424/88 |
| 4,695,459 | 9/1987 | Steinman et al. | 424/95 |
| 4,738,927 | 4/1988 | Taniguchi et al. | 435/69.52 |
| 4,904,481 | 2/1990 | Fathman | 424/85.91 |

FOREIGN PATENT DOCUMENTS

| | | |
|---|---|---|
| 0240344 | 10/1987 | European Pat. Off. |
| 89907436.3 | 6/1991 | European Pat. Off. |

OTHER PUBLICATIONS

Fahey et al., Annal. of Internal Med, 106, 1987, pp. 257-274.
Hwang et al. (1987) Cell 48:129.
Bishai et al. (1987) J. Bact. 169:1554.
Uchiyama et al. (1981) J. Immunol. 126:1393.
Lorberboum-Galski et al., Proc. Natl. Acad. Sci., USA, vol. 85, Mar. 1988, pp. 1922-1926.
Fidler, J. M. et al., Chemical Abstracts, vol. 78, No. 13, Apr. 2, 1973, pp. 315-316.
Leonard et al. (1983) P.N.A.S. U.S.A. 80:6957.
Gaulton et al. (1985) Clin. Immunl. and Immunopath. 36:18.
Kelley et al., "Anti-Interleukin 2 Receptor Antibody Suppresses Delayed-Type Hypersensitivity to Foreign and Syngeneic Antigens" (1986) Journal of Immunology, vol. 137, 2122-2124.
Kelley et al., "Anti-Interleukin 2 Receptor Antibody Suppresses Murine Diabetic Insulitis and Lupus Nephritis" (1988) Journal of Immunology, vol. 140, 001-003.
Kirkman et al., "The Effect of Anti-Interleukin-2 Receptor Monoclonal Antibody on Allograft Rejection", (1985) Transplantation, vol. 40, No. 6, pp. 719-722.
Gaulton et al., "Characterization of a Monoclonal Rat Anti-mouse Interleukin 2 (IL-2) Receptor Antibody and Its Use in the Biochemical Characterization of the Murine IL-2 Receptor", (1985), vol. 40, pp. 18-29.
Schneider et al., "Development of Suppressor Lymphocytes During Acute Rejection of Rat Cardiac Allografts and Preservation of Suppression by Anti-IL-2-Receptor Monoclonal Antibody" (1986) Transplantation, vol. 42, No. 2 pp. 191-196.
Volk et al., "Suppression of the local grafts-vs.-host reaction in rats by treatment with a monoclonal antibody specific for the interleukin 2 receptor" (1986) Eur. J. Immunol. 16:1309-1312.
Kupiec-Weglinski et al., "Interleukin-2 Receptor Targeted Therapy in Organ Transplantation" American College of Surgeons 1986 Surgical Forum vol. XXXVII, pp. 374-377.
Kelley et al., "Immunosuppression by Anti-Interleukin-2 Receptor Antibody but Not Anti-L3T4 Requires Terminal Complement Components" Transplantation Proceedings, vol. XIX, No. 1, 1987 p. 617.
Kupiec-Weglinski et al., "Anti-Interleukin-2 Receptor (IL-2R) Antibody Against Rejection of Organ Grafts" Transplantation Proceedings, vol. XIX, No. 1, 1987, pp. 591-593.
Kelley et al., "Inhibitory Effects of Anti-Interleukin 2 Receptor and Anti-L3T4 Antibodies on Delayed Type Hypersensitivity: The Role of Complement and Epitope", The Journal of Immunology (1987) vol. 138, 2771-2775.
Strom et al., "Toward More Selective Therapies to Block Undesired Immune Responses", Kidney International, vol. 35 (1989), pp. 1026-1033.
Hahn et al., "Curing BB rats of freshly manifested diabetes by short-term Treatment with a combination of a monoclonal anti-interleukin 2 receptor antibody and a subtherapeutic dose of cyclosporin A", Eur. J. Immunol. 1987, 17: 1075-1078.
Hahn et al., "Prolongation of rat pancreatic islet allograft survival by treatment of recipient rats with monoclonal anti-interleukin-2 receptor antibody and cyclosporin", Diabetologia (1987) 30P:44-46.

(List continued on next page.)

Primary Examiner—Garnette D. Draper
Attorney, Agent, or Firm—Fish & Richardson

[57] ABSTRACT

A method of inducing tolerance to a foreign antigen in a mammal, by administering an IL-2-receptor-positive-cell-destroying amount of a substance capable of destroying IL-2-receptor-positive cells which are newly activated in response to the antigen, to a degree which supresses the mammal's humoral immune response to a subsequent challenge with the antigen.

14 Claims, No Drawings

OTHER PUBLICATIONS

Kupiec-Weglinski et al., "Selective immunosuppression with anti-interleukin 2 receptor-targeted therapy: helper and suppressor cell activity in rat receipients of cardiac allografts" Eur. J. immunol. 1987, 17:313-319.

Soulillou et al., "Prevention of Rejection of Kidney Transplants by Monoclonal Antibody Directed Against Interleukin 2", The Lancet, 1987, pp. 1339-1342.

Tilney et al., "Synergy Between Subtherapeutic Doses of Cyclosporine and Immunobiological Manipulations in Rat Heart Graft Recipients". (1988), in press.

Peyronnet et al., "Prophylactic Use of a Monoclonal Antibody (33B3.1) Directed against Interleukin 2 Receptor Following Human Renal Transplantation", Transplantation Proceedings, (1988), in press.

Williams et al., (1987), "Diphtheria Toxin Receptor Binding Domain Substitution with Interleukin-2: Genetic Construction and Properties of a Diphtheria Toxin-Related Interleukin-2 Fusion Protein," Prot. Engin. 1: 493-498.

INDUCTION OF TOLERANCE TO A FOREIGN ANTIGEN IL-2 RECEPTOR-BINDING SUBSTANCES

Funding for the work described herein was provided by the federal government, which has certain rights in the invention.

This application is a continuation-in-part of U.S. patent application Ser. No. 196,036, filed May 19, 1988, now abandoned.

BACKGROUND OF THE INVENTION

This invention relates to the prevention of unwanted immune responses to foreign antigens.

Foreign antigens (e.g., recombinant proteins) administered to mammals, e.g., humans, for therapeutic purposes can cause unwanted immune responses, i.e., the formation of antibodies against the foreign antigen. Such immune responses can occur even where the antigen is the recombinant form of a naturally-occurring human protein, e. g., tissue plasminogen activator, because such a protein, even if having the same amino acid sequence as the natural protein, can be glycosylated in such a way as to cause the protein to appear foreign to the immune system. Thus, the term "foreign antigen" as used herein refers to any substance which is not identical to a substance naturally present in the mammal being treated. A goal of medicine is to be able to administer foreign therapeutic agents such as recombinant proteins, without evoking an unwanted immune response, i.e., to induce tolerance to the therapeutic agent. (Tolerance as used herein means the suppression of the ability to mount a humoral immune response to a foreign antigen upon re-challenge with that antigen, even after the substance inducing the suppression has been cleared from the bloodstream.)

SUMMARY OF THE INVENTION

In general, the invention features inducing, in a mammal, e.g., a human, tolerance to a foreign antigen administered to the mammal by administering to the mammal a substance capable of destroying interleukin-2 (IL-2)-receptor-positive cells which are newly activated in response to the antigen; the substance is administered simultaneously with or after (preferably within 7 days of and most preferably, simultaneously with) the administration of the foreign antigen, in an amount that destroys the IL-2-receptor-positive cells, and to a degree which suppresses the mammal's humoral immune response to a subsequent challenge with the antigen.

Preferably the IL-2-receptor-positive cells are helper T-cells, and the IL-2-receptor-positive-cell-destroying substance used in the method of the invention is a hybrid protein having a first and a second covalently joined proteinaceous portion, the first being the enzymatically active portion of a toxin molecule and the second being a protein or fragment thereof which is capable of binding specifically to an IL-2 receptor (i.e., binds to IL-2 receptor-positive cells to the substantial exclusion of non-IL-2-receptor-positive cells). Preferably the two portions are joined by a peptide bond and the IL-2-receptor-specific portion is IL-2 or an IL-2-receptor-binding fragment or analog thereof. The toxin molecule preferably is a bacterial toxin, most preferably, diphtheria toxin or, alternatively, Pseudomonas exotoxin.

Preferably, tolerance is permanent; re-challenge with the foreign antigen, at any time, even after the substance has cleared from the mammal's bloodstream, results in a suppression of the mammal's ability to mount a humoral immune response to the antigen. The antigen-specific induced state of tolerance achieved according to the invention can greatly improve disease-related therapy, e.g., short-term or long-term therapy involving administration of a monoclonal antibody, a recombinant protein, or other medically useful foreign antigens.

DESCRIPTION OF THE PREFERRED EMBODIMENTS

Tolerance to the foreign antigen trinitrobenzenesulfonic acid (TNBS) was defined as the inability of a mammal, after being re-challenged with a normally immune response generating (i.e., antibody-stimulating) dose of TNBS thirty days following administration of both TNBS and the tolerance inducing substance, to mount a humoral response to the re-challenge, as demonstrated by the absence in the mammal's bloodstream of circulating anti-TNBS antibodies following re-challenge.

Tolerance was achieved and demonstrated generally according to the following steps: 1) obtaining the tolerance-inducing substance; 2) immunization of the test mammals (mice) with TNBS; 3) administration of the tolerance-inducing substance to the test mammals; 4) re-challenge of the test mammals with TNBS; 5) determination of the normal response of tolerance-inducing-substance treated test mammals to a variety of antigens administered to the animals asynchronously with tolerance inducing substance; and 6) characterization of the immune response or lack thereof, following re-challenge, by quantitation of anti-TNBS antibodies and characterization of T-lymphocyte surface markers.

Preparation of Chimeric IL-2-toxin Fusion Protein

One embodiment of the invention employs, as the IL-2-receptor-positive-cell-destroying substance, a chimeric IL-2-receptor-specific toxin. Expression of the IL-2-receptor is a necessary, albeit transient, step in the common pathway of T-cell activation, and thus the IL-2 receptor is found on newly-activated helper T-cells, but not on older activated T-cells and resting T-cells.

The 68,086 dalton fusion protein, IL-2-toxin, was expressed from a genetically constructed hybrid gene encoding both a portion of diphtheria toxin and IL-2, in which DNA coding for the diphtheria toxin's generalized eukaryotic receptor binding domain was replaced with IL-2-encoding DNA, using recombinant DNA methods, as described in Murphy U.S. Pat. No. 4,675,382, hereby incorporated by reference. The genetic construction was carried out as follows, under the direction of John R. Murphy, University Hospital, Boston, Mass.

The diphtheria toxin-related portion of the fusion gene was carried on plasmid pABC508 (Bishai et al, 1987, J. Bacteriol. 169:1554). This plasmid carries the genetic information encoding the diphtheria tox promoter and the tox structural gene through amino acid $Ala_{485}$. The region of the tox gene encoding $Val_{483}$-$His_{484}$-$Ala_{485}$ is also defined by a unique SphI restriction endonuclease site. The IL-2 portion of the fusion gene was synthesized in vitro and cloned in the pUC18 vector (pUC18 can be obtained from Bethesda Research Labs, Bethesda, Md.). The sequence of the IL-2 gene is well known and is given in Taniguchi at al. U.S. Pat. No. 4,738,927, hereby incorporated by reference. By design, the 5'-end of the synthetic IL-2 gene was defined by an SphI restriction site on plasmid pDW15 in order to facilitate construction of the toxin/growth factor fusion gene. The chimeric diphtheria toxin-related IL-2 fusion gene was constructed by digestion of pDW15 with SphI and SalI, purification of the 428-bp synthetic IL-2 gene by agarose gel electrophoresus, and recloning of the fragment into SphI and SalI-digested pABC508. The SphI restriction site on the 5'-end of the synthetic IL-2 gene was positioned such that the translational reading frame would be retained through the diphtheria toxin/IL-2 fusion junction, such that $Pro_2$ of the mature form of IL-2 would be joined to $Ala_{485}$ of diphtheria toxin through a peptide bond.

Following ligation and transformation, several clones of *E. coli* were isolated that contained plasmids which had the restriction endonuclease digestion patterns expected for the toxin-growth factor gene fusion. One of these strains was selected and the recombinant plasmid designated pABI508. In order to ensure that the correct translational reading frame was maintained for the IL-2 portion of the gene fusion following assembly of the intact chimeric toxin gene, the nucleotide sequence of the IL-2 portion of the chimera through the fusion junction into the toxin portion of the recombinant gene was determined. The DNA sequence and the deduced amino acid sequence in the region of the toxin/T-cell growth factor fusion junction demonstrated that the IL-2 reading frame was retained.

Expression and Partial Purification of IL-2-toxin

Cloned diphtheria tox gene products possessing a functional signal sequence are expressed and exported to the periplasmic compartment of *E. coli* K-12. *E. coli* (pABI508) was grown in 10-L volumes and periplasmic extracts were prepared and analyzed by polyacrylamide gel electrophoresis and immunoblotting. A single protein of $M_r 68,000$ was found to be immunoreactive with monoclonal antibodies to recombinant IL-2 (rIL-2).

Anti-IL-2 was used as an immunoaffinity matrix for the purification of IL-2 toxin. Concentrated periplasmic extracts from *E. coli* (pABI508) were applied to an anti-IL-2 column, the column was exhaustively washed, and IL-2-toxin was eluted with 4M guanidine hydrochloride. Typically, immunoaffinity chromatography results in preparations of IL-2-toxin which are 50–70% pure as measured by laser densitometry of SDS-polacrylamide gels which have been Coomassie Blue stained.

Induction of Tolerance Using IL-2-toxin

Animals: BALB/c mice were obtained from the Jackson Laboratory, Bar Harbor, Me., and then maintained in the animal facilities at Brigham and Women's Hospital, Boston, Mass. All mice studied were males between 5 and 10 wks of age.

Immunization of Mice with Hapten: Mice were immunized with a 10 mm solution of TNBS in 0.5M phosphate-buffered saline (PBS) at pH 7.2 to 7.4 administered by subcutaneous injection of 0.1 ml bilaterally in the dorsum. 7 days after immunization, these mice were challenge with 25 µl of the same solution into the right footpad. 30 days after immunization, these animals were re-challenged with 0.1 ml of the same solution administered by subcutaneous injection bilaterally into the dorsum.

Administration of IL-2-Toxin

IL-2-toxin is selectively cytotoxic for both murine and human T cells bearing high affinity surface IL-2 receptors, whereas cells which do not express such receptors are resistant to IL-2-toxin action. Mice were injected intraperitoneally (IP) at daily intervals from the time of immunization through day 7 with a single dose of IL-2-toxin (5 µg per animal) or CRM45, a control substance (5 µg per animal) consisting of a 45,000 dalton molecular weight non-toxic mutant form of diphtheria toxin which lacks the toxin's normal receptor binding domain.

Characterization of IL-2-Toxin Induced Tolerance

In order to characterize the action of IL-2-toxin induced tolerance, two assays were performed: first, the mono-dispersed lymph node cells of the limb ipsilateral to antigen challenged footpad were phenotyped with T-cell subset and p55 IL-2R markers, using M7/20 monoclonal antibody to detect the p55 IL-2 receptor cell surface marker; and, second, circulating anti-TNBS antibodies were measured using an ELISA assay.

Two monoclonal antibodies were used for detecting T-cell surface markers, the M7/20 monoclonal antibody that is specific for the p55 subunit of the IL-2 receptor, and a control monoclonal antibody, RA3-2C2, that is specific for pre-B cells and some resting B cells, and therefore will not detect the newly activated IL-2 receptor positive cells. These monoclonal antibodies were prepared according to the following method.

Preparation and Administration of Monoclonal Antibodies

Production and initial screening of monoclonal antibodies to yield those specific for the IL-2 receptor can be carried out as described in Uchiyama et al., 1981, J. Immunol. 126:1393. This method, briefly, is as follows.

Human cultured T-lymphocytes are injected into mammals, e.g., mice, the spleens of the immunized animals are removed, and the spleen cells separated and then fused with immortal cells, e.g., mouse or human myeloma cells, to form hybridomas. The hybridoma culture supernatants are then screened for those that contain antibodies specific for the IL-2 receptor, using a complement-dependent cytotoxicity test. Human T-lymphocytes and EBV transformed B-lymphocytes are labeled with $^{51}Cr$ sodium chromate and used as target cells. When the target cells are incubated with antibody-containing culture supernatants in the presence of complement, only those cells that are bound by antibody will lyse and release $^{51}Cr$. The supernatants are collected and the amount of $^{51}Cr$ present is determined using a gamma counter. Those supernatants exhibiting toxicity against newly activated (i.e., IL-2 receptor bearing) T-lymphocytes, but not older activated T- or B-lymphocytes, are selected, and then subjected to a further screening step to select those supernatants that contain antibody that is specifically reactive with the IL-2 receptor; such antibody will immunoprecipitate the 50 kilodalton glycoprotein IL-2 receptor (described in detail in Leonard et al., 1983, P.N.A.S. USA 80:6957). The desired anti-IL-2 receptor antibody is purified from the supernatants using conventional methods.

The monoclonal antibody employed was antibody M7/20, which is described in Gaulton et al. (1985) Clin. Immunol. and Immunopath 36:18. M7/20 is a monoclonal rat anti-mouse K, mu, Ig antibody specific for the IL-2 receptor. M7/20 was purified from the culture supernatants of cells grown in serum free media (Hanna Labs, Berkeley, Calif.). Supernatants were precipitated with 40-50% saturated ammonium sulfate, dialyzed, passed over DEAE Affi-Gel Blue (Bio-Rad, Richmond, Va.) in 20 mM NaCl, and the eluate fractionated on Sephadex G-200 (Pharmacia, Piscataway, N.J.), run in 20 mM Tris (pH 7.2), 250 mM NaCl, 0.5% n-butanol. Antibody purity was assessed by SDS-Page gel electrophoresis. The control monoclonal antibody, RA3-2C2, was purified from cells obtained from the American Type Culture Collection (Rockville, Md.) by the procedure described above.

Phenotyping of Lymph Node Cells: Single cell ($10^6$ cells/sample) suspensions of draining paraortic lymph nodes of the 7 day TNBS-challenged lymph or spleen cells from IL-2-toxin-treated and control mice were stained with a saturating amount of either anti-L3T4 (prepared from the hybridoma GK15, American Type Culture Collection Accession No. T1B207, Rockville, Md.), a rat IgG2b Mab, or anti-Lyt-2 (from the hybridoma 53-6.72, A.T.C.C. Accession No. T1B195), a rat IgG2a, in 50 $\mu$l of PBS at pH 7.4 containing 20% heat-inactivated mouse serum (Cappel Laboratories, West Chester, Pa.), together with 0.1% sodium azide (PBS-S). The cells were counterstained with a fluorescein labeled rabbit anti-rat IgG (Cappel Laboratories) in 50 $\mu$l of PBS-S. Biotinylated purified M7/20 was then added to the cell preparation (50 $\mu$l) in PBS-S and counterstained with phycoerythrin-avidin in PBS-S (Becton-Dickinson, Mountain View, Calif.). All incubations were performed on ice for 30 min, and the cells were washed 3x in cold PBS and kept at 4° C. in the dark until analysis. The cells were analyzed on a FACS-1 cell analyzer (Becton-Dickinson FACS Systems, Mountainview, Calif.) using a Consort 30 computer program supplied by Becton-Dickinson. Background staining was determined by incubating cells with FITC rabbit anti-rat Ig followed by biotin labeled sheep anti-rat Ig and phycoerythrin-avidin.

IL-2-toxin selectively targeted and eliminated IL-2 receptor bearing T cells in draining lymph nodes. As determined by dual beam flow cytometric analysis the percent of CD4+ p55+ IL-2R+ cells was reduced from 14% in immunized, untreated mice to 5% in TNBS-immunized IL-2-toxin treated animals by day 7. Similarly, the CD8+ p55+ IL-2R+ cells were depleted from 18% to 5% by day 7. Indeed, IL-2-toxin was so effective that it reduced the number of p55+ IL-2R+ T cells to values similar to the levels detected in non-immunized mice (3% for CD4+ and 2% for CD8+ cells). By contrast, essentially no increase was detected in IL-2 receptor expression in spleen cells after TNBS immunization in IL-2 toxin treated mice, and the low percentage of IL-2R+ cells was not significantly different from non immunized animals.

Quantitation or Circulating Antibodies

In order to measure the extent to which IL-2-toxin treatment induced a state of tolerance with respect to humoral immunity, circulating antigen-specific antibodies were quantitated from serum obtained from mice on days 0, 7, and 30. The titer of anti-TNBS immunoglobulins present in the serum of IL-2 toxin-treated, TNBS-immunized mice was measured by a solid phase enzyme-linked immunoassay (ELISA). Polystyrene 96-well microtiter plates (COSTAR, Cambridge, Mass.) were coated with 40 ng of purified TNBS (50 $\mu$l/well) in a borate buffer (0.05M, pH 8.6) overnight at 4° C. Plates were then incubated with 3% bovine serum albumin (BSA) in PBS for 1 hr at 25° C. Four fold dilutions of mouse serum ranging from 1:50 to 1:12,800 suspended in 1% BSA, 0.05% Tween-80, PBS (diluting buffer) (50 $\mu$l) were then added to each well for 4 hrs at 25° C. The wells were then washed with (100 $\mu$l) PBS 1% Tween-80x1 and PBSx2. Bound serum IgG was detected by incubating the wells with Protein A-alkaline phosphatase conjugate (ZYMED) (1:3,000 dil.) in diluting buffer overnight at 4° C. After the plates were washed, bound alkaline phosphatase conjugate was detected by the addition of 1 mg/ml p-nitrophenyl phosphate (Sigma). The optical density (OD) was read at a wavelength of 405 nm. in a DYNASCAN miltichannel ELISA reader. All tests were performed in triplicate. The end titer was quantitated as the greatest dilution of test mouse serum which possessed significant binding to TNBS in excess of preimmune serum.

IL-2-toxin treatment induced tolerance to the TNBS antigen in TNBS immunized animals. Thirty days after immunization, exposure to TNBS did not stimulate an immune response to this antigen; there were no detectable levels of circulating anti-TNBS antibodies in the IL-2-toxin treated group.

Mechanism of Tolerance

The mechanism underlying the loss of the ability to respond to a foreign antigen, i.e., the induction of tolerance, is unknown, but may be a deletion of the antigen-specific clone of helper T-cells. The permanence of this clonal deletion may be the result of an attempt by the immune system to replenish this antigen-specific T-cell clone from the stem cell population of the bone marrow, resulting in a new antigen-specific clone of suppressor T-cells rather than helper T-cells.

Human Dosage and Administration

Dosages of tolerance inducing substances will vary, depending on factors such as half-life of the substance, potency, and route of administration, and the condition of the patient. Generally, IL-2-toxin should be administered to the patient in such a way that it is present in the vicinity of the foreign antigen at a concentration of about $10^{-9}$M IL-2-toxin, throughout the first 45 minutes of treatment with the foreign antigen. For example, where the foreign antigen is to be introduced into an adult patient's bloodstream, simultaneous intravenous infusion of a solution of approximately 15 mg IL-2-toxin in an appropriate volume of saline, delivered over the course of one hour, would generally provide an adequate concentration of IL-2-toxin in the blood for an adequate length of time. This protocol may be adjusted to provide for a lower concentration of IL-2-toxin for a longer period, or a higher concentration for a shorter period of treatment. Where the presence of the foreign antigen will be localized rather than systemic, the IL-2-toxin treatment protocol may be appropriately adjusted to provide for $10^{-9}$M IL-2-toxin in the immediate vicinity of the foreign antigen, for 45 minutes.

Other Embodiments

Other embodiments of the invent on are within the following claims. For example, the *Pseudomonas aeruginosa* exotoxin may be fused to the IL-2 receptor specific fragment in place of the diphtheria toxin portion of the hybrid protein. The Pseudomonas exotoxin is a well-known toxin, described in Pastan et al., U.S. Pat. No. 4,545,985, hereby incorporated by reference. The gene encoding this toxin is described in Hwang et al., (1987) Cell 48:129.

We claim:

1. A method of inducing, in a mammal, tolerance to an antigen administered to said mammal, the method comprising the step of administering to said mammal, after or simultaneously with the administration of said antigen, an effective amount of an IL-2-toxin hybrid molecule or an anti-IL-2-receptor antibody that selectively targets and destroys cells newly activated and expressing IL-2 receptors in response to said antigen, so that said mammal's humoral immune response to a subsequent challenge with said antigen is suppressed.

2. The method of claim 1 wherein said cells are helper T-cells.

3. The method of claim 1 wherein administration of said IL-2-toxin hybrid molecule or anti-IL-2 receptor antibody is carried out within 7 days after the administration of said antigen.

4. The method of claim 1 wherein administration of said IL-2-toxin hybrid molecule or anti-IL-2 receptor antibody is carried out simultaneously with the administration of said antigen.

5. The method of claim 1 wherein said IL-2-toxin hybrid molecule comprises a first and a second proteinaceous portion joined together covalently, said first portion comprising the enzymatically active portion of a toxin molecule and said second portion comprising a protein capable of specifically binding to an IL-2 receptor.

6. The method of claim 5 wherein said first and second portions are joined together by a peptide bond.

7. The method of claim 5 wherein said protein is IL-2 that binds to an IL-2 receptor expressed on said cells.

8. The method of claim 5 wherein said toxin molecule is a bacterial toxin.

9. The method of claim 8 wherein said toxin molecule is diphtheria toxin.

10. The method of claim 8 wherein said toxin molecule is Pseudomonas exotoxin.

11. The method of claim 1 wherein said anti-IL-2-receptor antibody is a monoclonal antibody.

12. A method of inducing, in a mammal, tolerance to an antigen administered to said mammal, the method comprising the step of administering to said mammal, after or simultaneously with the administration of said antigen, an effective amount of an IL2-toxin hybrid molecule so that said mammal's humoral immune response is suppressed to a subsequent challenge with said antigen.

13. The method of claim 12, wherein said hybrid molecule is a conjugate of IL2-diphtheria toxin.

14. The method of claim 12, wherein said hybrid molecule is a conjugate of IL2-Pseudomonas exotoxin A.

* * * * *